US010092492B2

(12) United States Patent
Terrisse et al.

(10) Patent No.: US 10,092,492 B2
(45) Date of Patent: Oct. 9, 2018

(54) COSMETIC COMPOSITION COMPRISING SPICULISPORIC ACID AND AT LEAST ONE SURFACTANT

(71) Applicant: L'OREAL, Paris (FR)

(72) Inventors: Isabelle Terrisse, Vitry sur Seine (FR); Caroline Sirichandra, Joinville le Pont (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/034,752

(22) PCT Filed: Nov. 7, 2014

(86) PCT No.: PCT/EP2014/074096
§ 371 (c)(1),
(2) Date: May 5, 2016

(87) PCT Pub. No.: WO2015/067779
PCT Pub. Date: May 14, 2015

(65) Prior Publication Data
US 2016/0310396 A1    Oct. 27, 2016

(30) Foreign Application Priority Data

Nov. 8, 2013  (FR) ..................... 13 60979

(51) Int. Cl.
A61K 8/49        (2006.01)
A61K 8/06        (2006.01)
A61K 8/19        (2006.01)
A61K 8/39        (2006.01)
A61K 8/44        (2006.01)
A61K 8/55        (2006.01)
A61K 8/60        (2006.01)
A61Q 19/00       (2006.01)
A61K 8/34        (2006.01)
A61K 8/37        (2006.01)
A61Q 1/00        (2006.01)
A61Q 5/02        (2006.01)
A61Q 19/10       (2006.01)

(52) U.S. Cl.
CPC .............. A61K 8/4973 (2013.01); A61K 8/06 (2013.01); A61K 8/19 (2013.01); A61K 8/345 (2013.01); A61K 8/37 (2013.01); A61K 8/39 (2013.01); A61K 8/44 (2013.01); A61K 8/442 (2013.01); A61K 8/553 (2013.01); A61K 8/60 (2013.01); A61K 8/602 (2013.01); A61K 8/604 (2013.01); A61Q 1/00 (2013.01); A61Q 5/02 (2013.01); A61Q 19/00 (2013.01); A61Q 19/10 (2013.01); A61K 2800/10 (2013.01); A61K 2800/49 (2013.01); A61K 2800/592 (2013.01); A61K 2800/596 (2013.01)

(58) Field of Classification Search
None
See application file for complete search history.

(56) References Cited

U.S. PATENT DOCUMENTS

| 6,830,746 | B2 * | 12/2004 | SaNogueira | A61K 8/27 424/400 |
| 2006/0116489 | A1 * | 6/2006 | Lennon | A61K 8/8158 525/479 |
| 2006/0222616 | A1 * | 10/2006 | Yoneda | A61K 8/39 424/70.14 |

FOREIGN PATENT DOCUMENTS

| JP | S60 31821 A | | 2/1985 |
| JP | 62030546 | * | 2/1987 |
| JP | H04-292695 A | | 10/1992 |
| JP | 2002-047137 A | | 2/2002 |
| JP | 2006-298864 A | | 11/2006 |
| JP | 2006-299163 A | | 11/2006 |
| KR | 10-2006-0111183 A | | 10/2006 |

OTHER PUBLICATIONS

Seppic Montanov 82, Mar. 2014.*
Science Lab, Potassium Hydroxide, Oct. 10, 2005.*
SciFinder, Spiculisporic Acid, retrieved online on Mar. 15, 2017.*
Ishigami et al., "Surface Active Properties of Biosoap from Spiculisporic Acid", Journal of Coltoid and Interface Science, vol. 94, No. 1, Jul. 1983.
M.J. Brown, "Biosurfactants for Cosmetic Applications", International Journal of Cosmetic Science 13, 61-64 (1991).
English Abstract for JP-S60 31821-A.
English Abstract for JP-2006-298864-A.
English Abstract for JP-H04-292695-A.
English Abstract for JP-2006-299163-A.
English Abstract for KR-10-2006-0111183-A.

* cited by examiner

Primary Examiner — Jennifer A Berrios
(74) Attorney, Agent, or Firm — Polsinelli PC

(57) ABSTRACT

The present invention relates to a cosmetic composition comprising, in a physiologically acceptable medium:
   an aqueous phase,
   spiculisporic acid,
   at least one non-sulfate and non-sulfonate surfactant, and
   at least one base,
   wherein the ratio $R_1$ of number of moles of base over the number of moles of spiculisporic acid is strictly greater than 1.

12 Claims, No Drawings

COSMETIC COMPOSITION COMPRISING SPICULISPORIC ACID AND AT LEAST ONE SURFACTANT

CROSS REFERENCE TO RELATED APPLICATIONS

This application is a National Phase filing under 35 U.S.C. § 371 of PCT/EP2014/074096 filed on Nov. 7, 2014; and this application claims priority to Application No. 1360979 filed in France on Nov. 8, 2013 under 35 U.S.C. § 119. The entire contents of each application are hereby incorporated by reference.

The present invention relates to novel stable cosmetic compositions comprising spiculisporic acid and/or one of its salts. The invention also relates to the cosmetic use of compositions as a make-up product, cleansing product, hygiene and/or care product for skin and/or hair.

Spiculisporic acid, also known under the name of 4,5-dicarboxy-4-pentadecanolide, has the following formula:

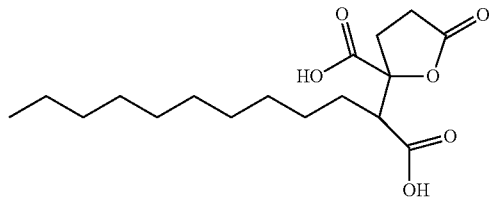 [SMILES: CCCCCCCCCCC(C(=O)O)C1(C(=O)O)CCC(=O)O1]

It is notably used as a surfactant.

From the state of the art it is known that at room temperature, spiculisporic acid (S-acid) is insoluble in water and fats but is soluble in ethanol. Spiculisporic acid is also described as being partly soluble in water at a high temperature. At room temperature, spiculisporic acid may be solubilized in water by salification. The possibility of forming three salts was shown; the sodium salts were characterized:

- S-1Na, the mono-sodium salt corresponding to the neutralization product of the carboxylic group down to the carbon in the C4 position of the S-acid;
- S-2Na, the di-sodium salt corresponding to the neutralization product of carboxylic groups bound to the carbons in the C4 and C5 positions of the S-acid;
- S-3Na, the tri-sodium salt corresponding to saponification of the lactone function of S-2Na.

These salts have distinct surfactant properties. The S-1Na and S-2Na forms, have surface activities suggesting a potential as surfactants.

On the other hand, and obviously, the lower the salification degree (close to the S-1Na form), the lower is the solubility. The solubility of spiculisporic acid in water, without opening the lactone function (S-3Na form) is obtained for pH values from about pH 5 to pH 7. Now, even in this optimized range, recrystallization of spiculisporic acid was observed, the latter being all the more substantial since the temperature is low. This is therefore incompatible with the marketing of cosmetic products which have to be stable over time, without any recrystallization.

Therefore there exists a need for cosmetic compositions comprising spiculisporic acid and/or one of its salts, and being stable over a wide range of temperatures.

The object of the present invention is to provide novel cosmetic compositions which are stable over time, based on spiculisporic acid.

According to an embodiment, the compositions of the invention are stable at 4° C. for 15 days, more preferably 1 month, or even for two months.

Within the present application, stable compositions are compositions wherein the spiculisporic acid remains solubilized and does not recrystallize. Such compositions remain limpid over time.

The present invention therefore relates to a cosmetic composition comprising, in a physiologically acceptable medium:
- an aqueous phase;
- spiculisporic acid,
- at least one non-sulfate and non-sulfonate surfactant, and
- at least one base, wherein the ratio $R_1$ of the number of base moles over the number of moles of spiculisporic acid is strictly greater than 1.

Therefore, the present invention relates to novel cosmetic compositions comprising the specific association of spiculisporic acid, of at least one non-sulfate and non-sulfonate surfactant, and at least one base.

Within the scope of the invention, and unless indicated otherwise, the aforementioned surfactant(s) is(are) different from spiculisporic acid and/or from one of its salts.

Within the scope of the invention, and unless indicated otherwise, the ratio $R_1$ corresponds to the ratio of the number of base moles over the number of moles of spiculisporic acid. This is therefore a molar ratio. Mention may for example be made of a molar ratio $R_1$ strictly greater than 1, and preferably less than or equal to 2.5. Thus, a molar ratio $R_1$ strictly greater than 1 corresponds to a number of base moles strictly greater than the number of moles of spiculisporic acid.

According to an embodiment, the ratio $R_1$ is strictly greater than 1. Preferably, the ratio $R_1$ is comprised between 1 and 2.5, and preferably ranging from 1.1 to 2. In particular, the ratio $R_1$ is equal to 2.

According to an embodiment, the ratio, designated as $R_2$, of the mass of spiculisporic acid over the mass of surfactant(s), different from the S-acid, is less than or equal to 12.5.

According to an embodiment, the ratio $R_2$ is comprised between 0.1 and 12.5. In particular, the ratio $R_2$ is comprised between 1 and 12.5. Preferably, the ratio $R_2$ is comprised between 1 and 5.

Within the scope of the invention, and unless indicated otherwise, the ratio $R_2$ corresponds to the ratio of the mass of spiculisporic acid over the mass of surfactant(s). This is therefore a mass ratio.

Surfactants

According to the invention, the non-sulfate and non-sulfonate surfactant may be a non-sulfate and non-sulfonate surfactant selected from the group consisting of amphoteric surfactants, anionic surfactants, non-ionic surfactants, cationic surfactants, and mixtures thereof.

This surfactant is not an anionic surfactant including a sulfate or sulfonate group.

Within the scope of the invention, and unless indicated otherwise, by "anionic surfactant comprising a sulfate group" is meant an anionic surfactant comprising an $-OSO_3^-$ or $-OSO_3H$ group (sulfate surfactant) and by "anionic surfactant comprising a sulfonate group" is meant one anionic surfactant comprising a group $-SO_3^-$ or $-SO_3H$ (sulfonate surfactant).

Within the scope of the invention, the «non-sulfate and non-sulfonate surfactant» is a non-sulfate surfactant (not comprising any sulfate group), a non-sulfonate surfactant (not comprising any sulfonate group) or a non-sulfate and non-sulfonate surfactant (not comprising any sulfate group and any sulfonate group).

According to the invention, the surfactant may be an amphoteric surfactant.

The amphoteric surfactants (this term including the amphoteric and zwitterionic surfactants) may for example be selected from (C8-C20)alkylbetaines, sulfobetaines (also called sultaines), (C8-C20)alkylsulfobetaines, (C8-C20) alkylamido(C1-C6)alkylbetaines, such as cocamidopropylbetaine, and (C8-C20)alkylamido(C1-C6)alkylsulfobetaines, amino acids such as glycine, (C8-C20)alkyl polyaminocarboxylates, (C8-C20)alkylamphoacetates, (C8-C20)alkylamphodiacetates, lecithins, salts thereof, and mixtures thereof.

As (C8-C20)alkylbetaines, mention may notably be made of cocobetain like the product marketed under the name of DEHYTON AB-30® by Cognis, laurylbetain like the product marketed under the name of GENAGEN KB® by Clariant, oxyethylene laurylbetain (10 EO), like the product marketed under the name of LAURYLETHER (10 EO) BETAIN® by Shin Nihon Rica, oxyethylene stearylbetain (10 EO) like the product marketed under the name of STEARYLETHER (10 EO) BETAIN® by Shin Nihon Rica.

Among the (C8-C20)alkylamido(C1-C6)alkylbetaines, mention may for example be made of cocamidopropyl betaine like the products marketed under the name of LEBON 2000 HG® by Sanyo, under the name of EMPIGEN BB® by Albright & Wilson, under the names of Tego Betain F 50 and CK D by EVONIK GOLDSCHMIDT, or further those marketed as a mixture with glyceryl laurate like the commercial references Tego Betain HS or Antil HS 60 from EVONIK GOLDSCHMIDT, lauramidopropyl betaine like the product marketed under the name of REWOTERIC AMB12P® by Witco. In a particular embodiment, (C8-C20)alkylamido(C1-C6)alkylbetaines are preferably chosen among (C8-C20)alkylamidopropylbetaines.

As sultains, mention may be made of (C8-C20)alkylsulfobetaines; alkyl(C8-C20)amidoalkyl(C1-C6) sulfobetaines, alkyl(C8-C20)amidoalkyl(C1-C6)hydroxyl sulfobetaines such as cocoyl-amidopropylhydroxy-sulfobetaine such as the one marketed under the name of CROSULTAIN C-50® by Croda.

As (C8-C20)alkyl polyaminocarboxylates (APAC), mention may be made of sodium cocoylpolyamino-carboxylate, such as the one marketed under the name of AMPHOLAK 7 CX/C®, and AMPHOLAK 7 CX® by AkzoNobel, sodium stearyl-polyamidocarboxylate such as the one marketed under the name of AMPHOLAK 7 TX/C by AkzoNobel, sodium carboxymethyloleyl-polypropylamine, such as the one marketed under the name of AMPHOLAK X07/C® by AkzoNobel. As C8-C20 alkyldiamphoacetates, mention may for example be made of N-di-sodium N-cocoyl-N-carboxymethoxyethyl-N-carboxymethyl-ethylenediamine (CTFA name: disodium cocamphodiacetate) like the product marketed under the name of MIRANOL C2M CONCENTRE NP® by Rhodia Chimie, and N-sodium N-cocoyl-N-hydroxyethyl-N-carboxymethyl-ethylenediamine (CTFA name: sodium cocamphoacetate) like the one sold by Evonik Goldschmidt under the name Rewoteric AM C.

As C8-C20 alkylamphodiacetates, mention may be made of disodium cocoamphodiacetate, disodium lauroamphodiacetate, disodium caproamphodiacetate, disodium caprylo-amphodiacetate, disodium cocoamphodipropionate, disodium lauroamphodipropionate, disodium caproamphodipropionate, disodium caproamphodipropionate, disodium caprylamphodipropionate, lauroamphodipropionic acid and cocoampho-idipropionic acid. Examples that may be mentioned include the cocoamphodiacetate sold by the company Rhodia under the trade name Miranol® C2M Concentrate.

Among lecithins, mention may be made of phospholipids and lysophospholipids. In particular, mention may be made of lecithins such as the product marketed by the NIKKOL group (Lecinol Series) or further lecithins marketed by CARGIL/LUCAS MEYER (the family of EMULMETIKS of EMULFLUIDS).

According to an embodiment, the amphoteric surfactant is selected from the group consisting of betaines, (C8-C20) alkylamido(C1-C6)alkylbetaines, glycine, sultains, C8-C20) alkyl polyaminocarboxylates, C8-C20 alkylamphoacetates, C8-C20 alkylamphodiacetates, lecithins, salts thereof and mixtures thereof.

According to an embodiment, the amphoteric surfactant is selected from the group consisting of (C8-C20)alkylbetaines, (C8-C20)alkylamido(C1-C6)alkylbetaines and preferably (C8-C20)alkylamidopropylbetaines, C8-C20 alkylamphoacetates, and mixtures thereof.

According to an embodiment, the surfactant is an amphoteric surfactant selected from the group consisting of cocoyl betain, cocamidopropylbetain, disodium cocoamphodiacetate, sodium cocoamphoacetate, and mixtures thereof.

According to an embodiment, the surfactant is cocamidopropylbetain or disodium cocoamphodiacetate.

According to the invention, the surfactant may be a non-sulfate and non-sulfonate anionic surfactant.

The anionic surfactants may notably be selected from anionic derivatives of proteins of vegetable origin, amino acids, (C6-C30)acylaminoacids, phosphates and (C6-C30) alkylphosphates, anionic (C8-C24)alkyl polyglucosides, soaps ((C8-C30)fatty acid salts), derivatives of soybean oil, lactic acid derivatives, glycyrrhizic acids or lipopeptides (like the biosurfactant Surfactin, a lipopeptide of microbial origin), salts thereof and mixtures thereof.

The anionic derivatives of proteins of vegetable origin are protein hydrolyzates with a hydrophobic group, said hydrophobic group may naturally be present in the protein or be added by reaction of the protein and/or of the protein hydrolyzate with a hydrophobic compound. The proteins are of vegetable origin, and the hydrophobic group may notably be a fatty chain with 8 to 30 carbon atoms, for example an alkyl chain including from 10 to 22 carbon atoms.

As anionic derivatives of proteins of vegetable origin, which may be used in the composition according to the invention, mention may more particularly be made of hydrolyzates of wheat, soybean, oat or silk proteins, including an alkyl chain having from 10 to 22 carbon atoms and salts thereof. The alkyl chain may notably be a lauryl chain and the salt may be a sodium, potassium and/or ammonium salt. For example mention may be made of sodium, potassium and/or ammonium salts of hydrolyzates of silk protein modified by lauric acid, such as the product marketed under the name of KAWA SILK by Kawaken; the sodium, potassium and/or ammonium salts of hydrolyzates of wheat protein modified by lauric acid, such as the potassium salt marketed under the name of AMINOFOAM W OR by Croda (CTFA name: potassium lauroyl wheat aminoacids) and the sodium salt marketed under the name of PROTEOL LW 30 by Seppic (CTFA name: sodium lauroyl wheat aminoacids); sodium, potassium and/or ammonium salts of hydrolyzates of oat protein including an alkyl chain having from 10 to 22 carbon atoms, and especially the sodium, potassium and/or ammonium salts of hydrolyzates of oat protein modified by lauric acid, such as a sodium salt marketed under the name of PROTEOL OAT (CTFA name: sodium lauroyl oat aminoacids), PROTEOL SAV 50S (INCI name: sodium cocoyl aminoacid), PROTEOL APL (INCI name: sodium cocoyl apple amino acids) by Seppic, AMARANTH S (INCI name: sodium cocoyl hydrolyzed amaranth proteins) and mixtures thereof.

As phosphates and C6-C30 alkylphosphates, mention may for example be made of monoalkylphosphates and dialkyl phosphates, such as lauryl mono-phosphate like the one marketed under the name of MAP 20® by Kao Chemicals, the potassium salt of dodecyl-phosphoric acid, a mixture of the mono- and di-ester (in majority di-ester) such as the one marketed under the name of CRAFOL AP-31® by Cognis, the mixture of mono-ester and of di-ester of octyl-phosphoric acid, such as the one marketed under the name of CRAFOL AP-20® by Cognis, the phosphoric acid and ethoxylated 2-butyloctanol (7 moles of EO) mono-ester and di-ester mixture, like the one marketed under the name of ISOFOL 12 7 EO-PHOSPHATE ESTER® by Condea, potassium C12-C13 alkyl phosphate like the one marketed under the references of ARLATONE MAP 230K-40®, triethanolamine C12-C13 alkylphosphate such as the one marketed under the name ARLATONE MAP 230T-60® by Uniqema, potassium lauryl phosphate like the one marketed under the name of DERMALCARE MAP XC-99/09® by Rhodia Chimie.

The C8-C24 alkyl-polyglucosides may notably be citrates, tartrates, carbonates and glycerol ethers obtained from C8-C24 alkyl polyglucosides. For example mention may be made of the sodium salt of cocoylpolyglucoside (1,4) tartaric ester, like the one marketed under the name of EUCAROL AGE-ET® by Cesalpinia, the sodium salt of cocoyl polyglucoside (1,4) citric ester like the one marketed under the name of EUCAROL AGE-EC® by Cesalpinia.

The soaps may be obtained from a fatty acid which is partly or completely saponified (neutralized) by a basic agent. These are soaps of alkaline or earth-alkaline metal or of organic bases. As fatty acids, it is possible to use saturated, linear or branched fatty acids including from 8 to 30 carbon atoms, and preferably including from 8 to 22 carbon atoms. This fatty acid may in particular be selected from palmitic acid, stearic acid, myristic acid, lauric acid, and mixtures thereof.

As basic agents, it is for example possible to use hydroxides of alkaline metals (sodium hydroxide and potassium hydroxide or potash), hydroxides of earth-alkaline metals (for example magnesium), ammonium hydroxide, or further organic bases such as triethanolamine, N-methylglucamine, lysine and arginine.

The soaps may notably be fatty acid alkaline salts, the basic agent being an alkaline metal hydroxide, and preferably potassium hydroxide or potash (KOH).

The amount of basic agent should be sufficient so that the fatty acid is at least partly neutralized.

Mention may notably be made of sodium or potassium laurate, potassium myristate, potassium palmitate, potassium stearate, potassium cocoate or further stearic acid salts of KOH formed in situ.

The derivatives of soybean oil and their salts are in particular the fatty acids with 8 to 30 carbons atoms and the fatty acid salts with 8 to 30 carbons atoms derived from soybean oil (the INCI name of which is «glycine soya oil» or «soybean oil») and in particular the salts of alkaline metals such as Na, Li, K, preferably Na or K, and of fatty acids with 8 to 30 carbons atoms derived from soya, such as potassium soyate like for example the one which is marketed by Noveon.

As C6-C30 acylaminoacids, mention may for example be made of:

C6-C30 acylglycinates, such as sodium cocoylglycinate, like the one marketed by Ajinomoto under the name of AMILITE GCS-12, and sodium cocoylglycinate like the one marketed by Ajinomoto under the name of AMILITE GCK-12, C6-C30 acyl glutamates such as disodium cocoyl glutamate like the one marketed by Ajinomoto under the name of AMISOFT ECS-22SB, sodium and disodium stearoyl glutamate like the one marketed by Ajinomoto under the names of AMISOFT HS21 P and HS11 Pf and sodium lauroyl glutamate like the one marketed by Ajinomoto under the name of AMISOFT LS11, C6-C30 acyl sarcosinate such as sodium lauroyl sarcosinate like the one marketed by Seppic under the name of ORAMIX L 30, sodium myristoyl sarcosinate, like the one marketed under the name of NIKKOL SARCOSINATE MN® by Nikkol, sodium palmitoyl sarcosinate, like the one marketed under the name of NIKKOL SARCOSINATE PN® by Nikkol; and sodium cocoyl sarcosinate like the one marketed by Zschimmer & Schwarz under the name of PROTELAN LS 9011/C.

C6-C30 acyl alaninates such as sodium N-lauroyl-N-methylamidopropionate, such as the one marketed under the name of SODIUM NIKKOL ALANINATE LN 30® by Nikkol or marketed under the name of ALANONE ALE® by Kawaken, and N-lauroyl N-methylalanine triethanolamine, like the one marketed under the name of ALANONE ALTA® by Kawaken C6-C30 acyl aspartate like the mixture of triethanolamine N-lauroylaspartate and of triethanolamine N-myristoylaspartate, like the one marketed under the name of ASPARACK® by Mitsubishi.

Mention may also be made of the sodium salt of lauroyl oat aminoacids such as PROTEOL OAT marketed by Seppic or the compound bearing the INCI name of sodium cocoyl aminoacids such as PROTEOL SAV 50S from Seppic.

Mention may also be made of alkaline salts of ($C_{10}$-$C_{22}$) acyl glutamic acids, preferably an alkaline salt of ($C_{12}$-$C_{20}$) acyl glutamic acids, and for example an alkaline salt of ($C_{16}$-$C_{18}$) acyl glutamic acids. The alkaline salts for example are sodium salts, potassium salts and lithium salts, and preferably sodium salts.

These may notably be one of the alkaline salts of stearoyl glutamic acid, of lauroyl glutamic acid, of $C_{16}$ acyl glutamic acid, glutamic myristoyl acid, glutamic cocoyl acid or glutamic hydrogenated tallow acyl acid.

Preferably, this is an ionic surfactant selected from sodium stearoyl glutamate, disodium stearoyl glutamate, potassium stearoyl glutamate, sodium lauroyl glutamate, disodium lauroyl glutamate, potassium lauroyl glutamate, sodium cocoyl glutamate, sodium hydrogenated tallow acyl glutamate, and mixtures thereof and preferably, this is sodium stearoyl glutamate.

The derivatives of lactic acids or their salts may be selected from (C6-C30)acyl lactylic acid, their salts (lactylates) such as stearoyl lactylate such as for example the one marketed by Oleon NV under the name of RADIAMULS SL 2980; sodium stearoyl lactylate as for example proposed by Oleon NV under the name of RADIAMULS SL 2990, by Karlshamns AB under the name of AKOLINE SL, by Uniqema under the name of PRIAZUL 2134 or further by Dr Straetmans under the name of DERMOFEEL SL; sodium isostearoyl lactylate like the one marketed by Uniqema under the name of PRIAZUL 2133; sodium behenoyl lactylate for example marketed by Rita Corporation under the name of PATIONIC SBL; sodium cocoyl lactylate such as the one marketed by Rita under the name of PATIONIC SCL, sodium oleoyl lactylate, sodium lauroyl lactylate (PATIONIC 138C from Caravan), sodium caproyl lactylate (CAPMUL S8L-G from Abitec).

Mention may also be made of the mixture of sodium cocoamphoacetate, glycerin, lauryl glucoside, sodium cocoylglutamate, sodium lauryl glucose carboxylate, like the one marketed by Cognis under the reference PLANTAPON SF.

In particular, the anionic surfactant is selected from the group consisting of fatty carboxylates, (C6-C30)alkyl sarcosinates, (C6-C30)alkyl phosphates, (C6-C30)alkyl glutamates, (C6-C30)acyl glutamates, and mixtures thereof.

According to an embodiment, the surfactant is an anionic surfactant selected from the group consisting of disodium cocoyl glutamate, sodium lauryl sarcosinate, and mixtures thereof.

According to an embodiment, the surfactant is disodium cocoyl glutamate or sodium lauryl sarcosinate.

According to the invention, the surfactant may be a non-ionic surfactant.

The non-ionic surfactants may for example be selected from (C6-C30)alkyl polyglucosides (APG), (C6-C30)alkylpolypentosides, (C6-C30)alkylpolyxylosides, maltose (C6-C30)esters, sucrose (C6-C30)esters, polyglycerol (C6-C30) fatty acids, oxyalkylene sugar esters, esters of (C6-C30)fatty acid and polyethylene glycol, esters of (C6-C30)fatty acid and sorbitan, derivatives of glucamine such as ethyl-2 hexyl oxy-carbonyl N-methyl glucamine, and mixtures thereof.

As alkylpolyglucosides, those containing an alkyl group including from 6 to 30 carbon atoms, and preferably from 8 to 16 carbon atoms, and containing a hydrophilic group (glucoside) preferably comprising 1.2 to 3 saccharide units, are preferably used. Mention may for example be made of decylglucoside (Alkyl-C9/C11-polyglucoside (1.4)) like the product marketed under the name of MYDOL 10® by Kao Chemicals, the product marketed under the name of PLANTAREN 2000 UP® by Cognis, and the product marketed under the name of ORAMIX NS 10® by Seppic; caprylyl/capryl glucoside like the product marketed under the name of ORAMIX CG 110® by Seppic or PLANTACARE 810 P by Cognis; laurylglucoside like the products marketed under the names of PLANTAREN 1200 N® and PLANTACARE 1200® by Cognis; and coco-glucoside like the product marketed under the name of PLANTACARE 818/UP® by Cognis, cetostearyl glucoside optionally mixed with cetostearylic alcohol, for example marketed under the name of MONTANOV 68 by Seppic, under the name of TEGO-CARE CG90 by Goldschmidt and under the name of EMULGADE KE3302 by Henkel; arachidyl glucoside, for example in the form of a mixture of arachidic and behenic alcohols and arachidyl glucoside marketed under the name of MONTANOV 202 by Seppic; cocoylethylglucoside, for example in the form of the mixture (35/65) with cetyl and stearyl alcohols, marketed under the name of MONTANOV 82 by Seppic, C12-C20 alkyl glucosides such as those marketed as a mixture with C14-C22 fatty alcohols under the reference of MONTANOV L by Seppic.

The oxyalkylene sugar esters are notably polyethylene glycol ethers of fatty and sugar esters. These oxyalkylene sugar esters may for example be selected from oxyethylene glucose esters such as PEG-120 methyl glucose dioleate like the one marketed under the name of Glucamate DOE 120 by Amerchol.

The fatty acid and polyethylene glycol esters are preferably $C_{16}$-$C_{22}$ fatty acid esters including from 8 to 100 ethylene oxide units.

The fatty chain of the esters may notably be selected from stearyl, behenyl, arachidyl, palmityl, cetyl units and mixtures thereof, such as a cetearyl, and preferably a stearyl chain.

The number of ethylene oxide units may range from 8 to 100, preferably from 10 to 80, and better from 10 to 50. According to a particular embodiment of the invention, this number may range from 20 to 40.

As an example of a fatty acid and polyethylene glycol ester, mention may be made of stearic acid esters respectively comprising 20, 30, 40, 50, 100 units of ethylene oxide, such as the products respectively marketed under the name of Myrj 49 P (polyethylene glycol stearate 20 EO; CTFA name: PEG-20 stearate), Myrj 51, Myrj 52 P (polyethyleneglycol stearate 40 EO; CTFA name: PEG-40 stearate), Myrj 53, Myrj 59 P by CRODA.

The $C_{16}$-$C_{22}$ fatty acid and sorbitan esters are in particular $C_{16}$-$C_{22}$ acid and sorbitan esters and are formed by esterification of at least one fatty acid including at least one saturated or unsaturated linear alkyl chain, respectively having from 16 to 22 carbon atoms, with sorbitol. These esters may notably be selected from sorbitan stearates, behenates, arachidates, palmitates, oleates and mixtures thereof. Sorbitan stearates and palmitates are preferably used, and preferentially sorbitan stearates.

As an example of a sorbitan ester which may be used in the composition according to the invention, mention may be made of sorbitan monostearate (CTFA name: sorbitan stearate) like the one sold by Croda under the name of Span 60, sorbitan tristearate like the one sold by Croda under the name of Span 65 V, sorbitan monopalmitate (CTFA name: sorbitan palmitate) like the one sold by Croda under the name of Span 40, sorbitan monoleate like the one sold by Croda under the name of Span 80 V, sorbitan trioleate like the one sold by Uniquema under the name of Span 85 V. Preferably, the sorbitan ester used is sorbitan tristearate.

The sucrose and fatty acid esters are preferably selected from esters derived from the reaction of sucrose(s) (saccharose(s)) and of fatty acid(s) comprising from 10 to 24 carbon atoms, preferably from 12 to 20 carbon atoms, better from 12 to 18 carbon atoms and even better from 12 to 16 carbon atoms.

The fatty acids comprising from 10 to 24 carbon atoms may be linear or branched, saturated or unsaturated.

The fatty acids may be selected from oleic acid, lauric acid, palmitic acid, myristic acid, stearic acid, linoleic acid, capric acid, or mixtures thereof.

According to an embodiment, the sucrose and fatty acid ester is selected from the esters derived from the reaction of sucrose and of a fatty acid comprising from 12 to 18 carbon atoms, preferably from 12 to 16 carbon atoms such as lauric acid and/or palmitic acid like for example sucrose laurate, sucrose palmitate or a mixture thereof.

The sucrose and fatty acid esters may be selected from mono-, di-, tri- and tetra-esters, and mixtures thereof, preferably esters with a low esterification degree such as for example sucrose and fatty acid monoesters, diesters, triesters or a mixture thereof. The sucrose and fatty acid ester may appear as a mixture of esters with a low esterification degree such as for example a monoester and diester mixture or a monoester, diester and triester mixture.

In the case when a mixture of sucrose and fatty acid esters is used, a mixture is preferred in which the esters with a low esterification degree, in particular monoesters, are a majority and for example represent at least 50%, preferably at least 60% by weight of the mixture of sucrose and fatty acid esters.

In particular a mixture of sucrose and fatty acid esters comprising from 12 to 16 carbon atoms may be used, in particular a mixture of lauric acid or palmitic acid mono-, di- and tri-esters, said mixture may comprise as a minority (in a content of less than or equal to 40% by weight based on the weight of the sucrose, ester and fatty acid mixture) sucrose and fatty acid esters in which the fatty acid comprises more than 16 carbon atoms.

Preferably, the sucrose and fatty acid ester used in the present invention has an HLB greater than or equal to 10, preferably greater than or equal to 12.

As this is well known, by HLB (Hydrophilic-Lipophilic Balance) is meant the balance between the size and the force of the hydrophilic group and the size and the force of the lipophilic group of the surfactant.

The HLB value according to GRIFFIN is defined in J. Soc. Cosm. Chem. 1954 (volume 5), pages 249-256.

As examples of esters or of sucrose and fatty acid ester mixtures, mention may be made of:

Surfhope SE COSME C-1416, having an HLB of 16, which is a sucrose myristate comprising about 80% of monoester, the remainder of the mixture consisting of di- and tri-esters, Surf hope SE COSME C-1216 for which the INCI name is sucrose laurate, with an HLB equal to 16 and comprises from 75 to 90% of monoester, the remainder of the mixture consisting of di- and tri-esters, Surfhope SE COSME C-1215L for which the INCI name is sucrose laurate, with an HLB equal to 15, comprising about 70% of monoesters, the remainder of the mixture consisting of diesters and of other polyesters, Surf hope SE COSME C-1616, having an HLB of 16, which is a mixture of saccharose and palmitic and/or stearic acid esters (INCI name sucrose palmitate), comprising from 75 to 90% of monoester, the remainder of the mixture consisting of di- and tri-esters, and which may comprise a sucrose stearate and sucrose palmitate stearate.

Mention may also be made of the ester bearing the INCI name of sucrose laurate marketed by Dai-ichi Seiyaku under reference DK ester S-L18A, with an HLB equal to 17, comprising 70% of monoesters and 30% of di- and tri-esters.

Mention may also be made of, as examples of esters and of fatty acid sucrose ester mixtures:

the products sold under the names of F160, F140, F110, F90, F70, SL40 by CRODESTA, respectively designating sucrose palmito-stearates formed with 73% of monoester and 27% of di- and tri-ester, with 61% of monoester and 39% of di-, tri-, and tetra-ester, with 52% of monoester and 48% of di-, tri-, and tetra-ester, with 45% of monoester and 55% of di-, tri-, and tetra-ester, with 39% of monoester and 61% of di-, tri-, and tetra-ester, and sucrose mono-laurate;

the products sold under the name of RYOTO SUGAR ESTERS for example referenced as B370 and corresponding to saccharose behenate formed with 20% of monoester and 80% of di-triester-polyester;

sucrose mono-di-palmito-stearate marketed by GOLDSCHMIDT under the name of TEGOSOFT PSE.

According to an embodiment, sucrose laurate is used.

From among the non-ionic surfactants according to the invention, mention may also be made of saponins.

Saponins may preferably be selected from saponins extracted from soap trees (*Sapindus mukurossi, Sapindus trifoliatus, sapindus saponaria*), licorice (*Glycyrrhiza glabra*), horse chestnut (*Aesculus hippocastanum*), bacoppa (*Baccopa monneria*), Sarsaparilla (*Smilax medica, Smilax aspera, Smilax ornata*), soap bark tree (*Quillaja saponaria*), common soapwort (*Saponaria officinalis*), ginseng (*Panax ginseng*), yucca (*Yucca schidigera*), devil's thorn (*Tribulus terrestris*), Juazirine (*Zizyphus joazeiro*), Jiaogulan (*Gynostemma pentaphyllum*), shatavari (*Asparagus racemosus*), luzerne (*Medicago sativa*) and mixtures thereof.

Preferably, the non-ionic surfactant is selected from the group consisting of C6-C30 alkylpolyglucosides, preferably C8-C16 alkylpolyglucosides, C6-C30 alkylglycosides, esters of polyoxyethylene sorbitan and C12-C18 fatty acid, and mixtures thereof.

According to an embodiment, the surfactant is a non-ionic surfactant selected from the group consisting of decyl glucoside, coco-glucoside, sucrose laurate, sorbitol, polyoxyethylene (20 EO) sorbitan monolaurate (like the one sold by Evonik Goldschmidt under the name TEGO SML 20 (INCI name: Polysorbate 20), and mixtures thereof.

According to an embodiment, the surfactant is decyl glucoside or coco-glucoside.

According to an embodiment, the surfactant is a mixture of sucrose laurate and sorbitol.

According to another embodiment, the surfactant is polyoxyethylene (20 EO) sorbitan monolaurate (like the one sold by Evonik Goldschmidt under the name TEGO SML 20 (INCI name: Polysorbate 20).

The cosmetic compositions of the invention may comprise a single surfactant as defined above, or a mixture of surfactants as defined above.

In particular, the cosmetic compositions of the invention comprise a surfactant.

According to the invention, the total content of surfactant(s) (spiculisporic acid+additional surfactant) in the cosmetic composition of the invention may range from 0.1% to 30% by mass based on the total mass of said composition.

Preferably, the total content of surfactant(s) (spiculisporic acid+additional surfactant) according to the invention ranges from 0.5% to 15%, and preferentially from 1% to 10% by mass based on the total mass of said composition.

According to a preferred embodiment, the total content of surfactant(s) (spiculisporic acid+additional surfactant) according to the invention is comprised between 1% and 10%, preferably between 3% and 8%.

Base

Thus, the cosmetic compositions according to the invention may also comprise an organic or mineral base. The organic or mineral base may be a Bronsted-Lowry or Lewis base.

Particularly, the base(s) may be selected from:

a) alkanolamines, such as mono-, di- and tri-ethanolamines, isopropanolamine, 2-amino-2-methyl-1-propanol, b) oxyethylene and/or oxypropylene ethylene-diamines, c) mineral or organic hydroxides, d) alkaline metal silicates such as sodium metasilicates, e) preferably basic amino acids such as arginine, lysine, ornithine, citrulline and histidine, f) carbonates and bicarbonates, particularly of a primary, secondary, or tertiary amine, of an alkaline or earth-alkaline metal or of ammonium, and g) the compounds of the following formula (III):

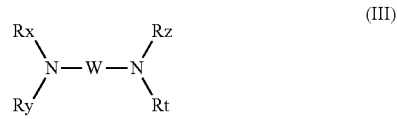

wherein W is a $C_1$-$C_6$ alkylene radical optionally substituted with a hydroxyl group or a $C_1$-$C_6$ alkyl group; Rx, Ry, Rz and Rt, either identical or different, represent a hydrogen atom, a $C_1$-$C_6$ alkyl group, a $C_1$-$C_6$ hydroxyalkyl group, or a $C_1$-$C_6$ aminoalkyl group.

As an example of such compounds of formula (III), mention may be made of 1,3-diaminopropane, 1,3-diamino-2-propanol, spermine or spermidine.

The mineral or organic hydroxides are preferably selected from hydroxides of an earth-alkaline metal, hydroxides from an earth-alkaline metal, such as sodium or potassium hydroxides, hydroxides of a transition metal, such as hydroxides of the metals of the Groups III, IV, V and VI of the Periodic Classification of the Elements, hydroxides of lanthanides or actinides, hydroxides of quaternary ammoniums, and guanidinium hydroxide.

The hydroxide may be formed in situ such as for example guanidine hydroxide, formed by reaction of calcium hydroxide with guanidine carbonate.

According to a particular embodiment of the invention, the base may be selected from the group of inorganic bases such as sodium hydroxide, potassium hydroxide, lithium hydroxide, cesium hydroxide, calcium hydroxide, magnesium hydroxide, zinc hydroxide, or similar bases, of a basic mineral salt and of a basic organic salt containing lithium, sodium, potassium, calcium, magnesium, ammonium, a basic amino acid like lysine, arginine, histidine, ornithine or the like, a basic oligopeptide having these amino acids as bases, basic amines such monoethanolamine, diethanolamine, 2-(dimethylamino)ethanol, triethanolamine, triisopropanolamine, diisopropanolamine, monoisopropanolamine, ammonia or similar bases, other organic bases such as guanidine carbonate and other similar bases and mixtures thereof.

In a particular embodiment, the base is a mineral base, preferably a mineral hydroxide base, even more preferably sodium or potassium hydroxide.

According to an embodiment, the base is potassium hydroxide.

Within the scope of the invention and unless specified otherwise, the base used is a neutralizing base, i.e., it allows neutralization of spiculisporic acid in order to form a salt of said acid. For example mention may be made of sodium, potassium, triethanolamine and arginine salt of spiculisporic acid.

According to an embodiment, the use of two moles of spiculisporic acid allows neutralization of two carboxylic functions of said acid without breaking the lactone function. In particular, two moles of base are used for one mole of spiculisporic acid in the aforementioned cosmetic compositions.

According to an embodiment, the use of potassium hydroxide allows the formation of the monopotassium salt, of the dipotassium salt, or of the tripotassium salt of spiculisporic acid.

According to the invention, the pH of the composition according to the invention may be comprised between 4 and 10. Preferably, the pH is comprised between 5 and 8, and in particular between 5 and 6.5.

According to the invention, the spiculisporic acid content may range from 0.1% to 15% by mass based on the total mass of said composition.

According to a preferred embodiment, the spiculisporic acid content is comprised between 0.1% and 15%, preferably between 0.5% and 10%, and preferentially between 1% and 8% by mass of active material based on the total mass of the composition.

Physiologically Acceptable Medium

In addition to the compounds indicated earlier, i.e., spiculisporic acid, at least one base, and at least one surfactant, a cosmetic composition according to the invention comprises a physiologically acceptable medium.

Within the scope of the invention, and unless specified otherwise, by a «physiologically acceptable medium», is meant a medium suitable for cosmetic applications, and notably suited to the application of a composition of the invention on the skin and/or the hair. The physiologically acceptable medium is generally adapted to the nature of the support on which the composition has to be applied, as well as to the aspect under which the composition has to be conditioned.

Aqueous Phase

The composition according to the invention comprises an aqueous phase. This aqueous phase notably comprises water and/or hydrophilic solvents like polyols.

The water used in the composition of the invention may be demineralized pure water but also mineral water and/or thermal water and/or seawater, i.e., the water of the composition may partly or totally be formed by water selected from mineral waters, thermal waters, seawaters and mixtures thereof. Generally, a mineral water is able to be consumed, which is not always the case of thermal water. Each of these waters inter alia contain solubilized minerals and/or trace elements. These waters are known for being used for specific treatment purposes depending on the trace elements and the particular minerals which they contain, such as hydration and desensitization of the skin or the treatment of certain dermatites. By mineral or thermal waters, are not only designated natural mineral or thermal spring waters but also natural, mineral or thermal spring waters enriched with mineral constituents and/or in additional trace elements, as well as mineral aqueous solutions and/or containing trace elements prepared from purified (demineralized or distilled) water.

A natural thermal spring or mineral water used according to the invention may for example be selected from the spring water from Vittel, the waters of the Vichy basin, the spring water from Uriage, the spring water from La Roche Posay, the spring water from La Bourboule, the spring water from Enghien-les-Bains, the spring water from Saint Gervais-les-Bains, the spring water from Néris-les-Bains, the spring water from Allevar-les-Bains, the spring water from Digne, the spring water from Maiziéres, the spring water from Neyrac-les-Bains, the spring water from Lons-le-Saunier, from Eaux Bonnes, the spring water from Rochefort, the spring water from Saint Christau, the spring water from Fumades and the spring water from Tercis-les-bains, the spring water from Avene.

The aqueous phase of the composition of the invention may comprise an organic solvent soluble in water at room temperature (25° C.), for example selected from lower mono-alcohols including from 2 to 6 carbon atoms and in particular 2 to 4 carbon atoms, such as ethanol, isopropanol, propanol, butanol, pentanol, hexanol, polyols with 2 to 20 carbon atoms, preferably 2 to 6 carbon atoms, such as for example glycerin, propylene glycol, isoprene glycol, butylene glycol, hexylene glycol, polyethylene glycols such as PEG-8, dipropylene glycol, diethylene glycol, and mixtures thereof.

According to a preferred embodiment of the invention, the polyol is glycerin which gives better comfort for the application. It is possible to add to glycerin, other polyols insofar that the qualities of the composition are maintained.

The amount of water in the aqueous phase may be greater than or equal to 10% by weight of the total mass of the composition, preferably greater than or equal to 30%, and better greater than or equal to 50%.

Preferably, the amount of water in the composition is comprised between 50% and 95% by weight of the total weight of the composition.

The amount of polyol(s) in the aqueous phase may for example range from 0.5% to 30% by weight, preferably from 0.5% to 15% by weight. In particular, this amount may range from 1% to 10% by weight, preferably from 2% to 10% by weight and more preferentially from 2% to 8% by weight based on the total weight of the aqueous phase.

Fatty Phase

The composition according to the invention may either comprise or not a fatty phase. When it is present, the fatty phase of the composition according to the invention comprises the whole of the fat-soluble or fat-dispersible compounds present in the composition, and in particular, the fats liquid at room temperature (25° C.) and at atmospheric pressure or oils (which form the oily phase).

The oils present in the composition according to the invention may be silicone or hydrocarbon oils.

By silicone oil, is meant an oil containing at least one silicon atom and notably containing Si—O groups.

As silicone oils, mention may for example be made of volatile silicone oils such as cyclopolydimethylsiloxanes (INCI name: cyclomethicone), such as cyclopentasiloxane, cyclohexasiloxane, octamethylcyclotetrasiloxane, decamethylcyclopentasiloxane, dodeca-methylcyclohexasiloxane; linear silicones such as heptamethylhexyl-trisiloxane, heptamethyloctyl-trisiloxane, hexamethyl-disiloxane, octamethyltrisiloxane, decamethyltetrasiloxane, dodecamethyl pentasiloxane; non-volatile silicone oils like polymethylsiloxanes (PDMS), and phenyl polymethylsiloxanes such as phenyltrimethicones, phenyldimethicones, phenyltrimethylsiloxydiphenyl-siloxanes, diphenyl-dimethicones, diphenylmethyldiphenyl trisiloxanes, 2-phenylethyltrimethyl-siloxy-silicates, and polymethylphenylsiloxanes; polysiloxanes modified by fatty acids, fatty alcohols or polyoxyalkylenes, and mixtures thereof.

By «volatile» is meant a compound which may evaporate in contact with the skin in less than one hour, at room temperature and at atmospheric pressure. Volatile oil is a volatile cosmetic oil, liquid at room temperature, notably having a non-zero vapor pressure, at room temperature and at atmospheric pressure, in particular having a vapor pressure ranging from 0.13 Pa to 40,000 Pa ($10^{-3}$ to 300 mmHg), and preferably ranging from 1.3 Pa to 13,000 Pa (0.01 to 100 mmHg), and preferentially ranging from 1.3 Pa to 1,300 Pa (0.01 to 10 mmHg).

By hydrocarbon oil, is meant an oil essentially formed, or even consisting of, carbon and hydrogen atoms, and optionally oxygen, nitrogen atoms and not containing any silicone or fluorine atom; it may contain ester, ether, amine, amide groups.

As oils which may be used in the composition of the invention, mention may for example be made of:
hydrocarbon oils of vegetable origin, such as squalane, liquid triglycerides of fatty acids including from 4 to 30 carbon atoms such as triglycerides of heptanoic or octanoic acids or further, for example jojoba, babassu, sunflower, olive, coconut, brazil nut, marula, maize, soya, pumpkin, grape pip, flax, sesame, hazelnut, apricot, macadamia, arara, coriander, castor, avocado oils, triglycerides of caprylic/capric acids like those marketed by Stearineries Dubois or those marketed under the names of Miglyol 810, 812 and 818 by Dynamit Nobel, shea butter oil;
synthetic esters and ethers notably of fatty acids, such as oils of formulae of $R^1COOR^2$ and $R^1OR^2$ wherein $R^1$ represents the remaining radical of a fatty acid or of a fatty alcohol including from 8 to 29 carbon atoms, and $R^2$ represents a hydrocarbon chain, either branched or not, containing from 3 to 30 carbon atoms, such as for example Purcellin oil, octyl-2-dodecyl stearate, octyl-2-dodecyl erucate, isostearyl isostearate; hydroxylated esters like isostearyl lactate, octylhydroxystearate, octyldodecyl hydroxystearate, diisostearyl-malate, triisocetyl citrate, heptanoates, octanoates, decanoates of fatty acids; polyol esters, such as propylene glycol dioctanoate, neopentylglycol diheptanoate and diethyleneglycol diisononanoate; and pentaerythritol esters such as pentaerythrytyl tetraisostearate;
linear or branched hydrocarbons of mineral or synthetic origin, volatile or non-volatile, and derivatives thereof, such as branched alkanes, including from 8 to 18 carbon atoms, for example $C_8$-$C_{18}$ iso-alkanes (also called isoparaffins) like isododecane, isodecane, isohexadecane, such as the isoparaffins sold under the commercial names of Isopar by Exxon Chemical or the oils sold under the commercial names of Permethyl by Presperse, isohexadecane and isododecane marketed by INEOS; as well as Vaseline oil and hydrogenated polyisobutene such as Parléam® oil marketed by Nof Corporation; volatile linear alkanes comprising from 7 to 17 carbon atoms like undecane, tridecane, such as the one described in examples 1 and 2 of patent application WO2008/155059 of Cognis;
fatty alcohols liquid at room temperature having from 8 to 26 carbon atoms, preferably 12 to 18 carbon atoms such as octyldodecanol, 2-butyloctanol, 2-hexyldecanol, 2-undecylpentadecanol or oleic alcohol; and
mixtures thereof.

Mention may in particular be made of the following oils:
the esters from the reaction of at least one fatty acid including at least 6 carbon atoms, preferably 6 to 26 carbon atoms and better from 6 to 20 carbon atoms, still better from 6 to 16 carbon atoms and of at least one alcohol comprising from 1 to 17 carbon atoms and better from 3 to 15 carbon atoms; mention may notably be made of isopropyl myristate, isopropyl palmitate, ethyl-2-hexyl caprate/caprylate (or octyl caprate/caprylate), ethyl-2-hexyl palmitate, isostearyl neopentanoate, isononyl isononanoate, hexyl laurate, esters of lactic acid with fatty alcohols comprising 12 or 13 carbon atoms, dicaprylyl carbonate as the one which is marketed under the name of Cetiol CC by Cognis,
fatty acid ethers comprising from 6 to 20 carbon atoms such as dicaprylyl ether (as the one sold under the trade name Cetiol EO from Cognis),
glycerol ethers comprising from 6 to 12 carbon atoms such as 2-ethyl hexyl ether of glycerol (INCI name: ethylhexylglycerin) such as Sensiva SC 50 from Schulke & Mayr GmbH;
octydodecanol, alkanes such as those which are described in the patent applications of Cognis, WO 2007/068371, or WO2008/155059, (mixtures of distinct alkanes which differ by at least one carbon). These alkanes are obtained from fatty alcohols, themselves obtained from coconut or palm oil.

As an example of linear alkanes suitable for the invention, mention may be made of n-heptane (C7), n-octane (C8), n-nonane (C9), n-decane (C10), n-undecane (C11), n-dodecane (C12), n-tridecane (C13), n-tetradecane (C14), and mixtures thereof. According to a particular embodiment, the volatile linear alkane is selected from n-nonane, n-undecane, n-dodecane, n-tridecane, n-tetradecane, and mixtures thereof.

According to a preferred embodiment, mention may be made of the mixtures of n-undecane (C11) and of n-tridecane (C13) obtained in Examples 1 and 2 of the WO2008/155059 application of Cognis;

the polyesters obtained by condensation of an unsaturated fatty acid with 4 to 36 carbon atoms and a diol dimer and/or trimer such as for example the polyesters of dilinoleic acid and of a diol with 2 to 6 carbon atoms marketed by Biosynthis under the name of Viscoplast and notably the polymer bearing the INCI name: dilinoleic acid/propanediol copolymer; and mixtures thereof.

Preferably, the oil is selected from vegetable oils as mentioned above.

The amount of fatty phase in the composition of the invention may range from 0% to 80% by weight, preferably from 01% to 60% by weight based on the total weight of the composition.

According to a particular embodiment of the invention, the amount of fatty phase in the composition is comprised between 0 and 5% by weight of the total weight of the composition.

Additives

A cosmetic composition according to the invention may also further comprise any additive usually used in the relevant field, for example selected from gums, resins, dispersants, semi-crystalline polymers, antioxidants, essential oils, preservatives, perfumes, neutralizers, antiseptic agents, UV protective agents, cosmetic actives, such as vitamins, moisturizing agents, emollients or collagen protective agents, and mixtures thereof.

Adjustment of the nature and of the amount of the additives present in the compositions according to the invention falls under the routine operations of one skilled in the art, so that the cosmetic properties and the desired stability properties of the latter are not affected.

Preparation of the Composition

According to an embodiment, the cosmetic composition according to the invention is prepared according to the following steps:

step a): preparation of an aqueous solution A of spiculisporic acid with a base;

optional step b): heating the aforementioned aqueous solution A;

step c): adding at least one aforementioned surfactant to the solution A at the end of step b) in order to lead to a solution B; and then step d): adding an organic phase miscible with water to the solution B.

According to an embodiment, the solution A comprises a salt of spiculisporic acid, synthesized from spiculisporic acid and from a selected base from among triethanolamine, L-arginine, NaOH and KOH. Preferably, the solution A comprises a potassium salt of spiculisporic acid, and notably the di-potassium salt of spiculisporic acid. The latter is notably prepared by a mixture between spiculisporic acid, water and KOH.

According to an embodiment, the cosmetic composition according to the invention is prepared according to the following steps:

step a): preparing an aqueous solution A of spiculisporic acid with a base;

step b): heating the aforementioned aqueous solution A;

step c): adding at least one aforementioned surfactant to the solution A at the end of step b) in order to lead to a solution B; and then step d): adding an organic phase miscible with water to the solution B.

According to an embodiment, step b) consists in heating the aqueous solution A to a temperature comprised from 30° C. to 90° C., preferably from 35° C. to 60° C., and preferentially at a temperature of about 40° C. This step advantageously allows acceleration of solubility.

According to an embodiment, the solution B obtained at the end of step c) comprises water, spiculisporic acid in a salified form, and at least one surfactant according to the invention.

According to an embodiment, the organic phase miscible with water added to the solution B comprises at least one organic solvent as mentioned above.

Uses

The cosmetic compositions according to the invention may be care, sunscreen, cleansing (makeup removal), hygiene or makeup products for the skin and/or the hair.

These compositions are therefore intended to be applied on the skin and/or the hair.

Thus, the present invention also relates to the non-therapeutic cosmetic use of an aforementioned cosmetic composition, as a makeup, hygiene, cleansing and/or care product for the skin and/or the hair.

According to an embodiment, the compositions of the invention are in the form of a foundation, a makeup remover, a care product for the face and/or the body and/or the hair, of an anti-ageing care product, of a sunscreen, of a fatty skin care product, of a whitening care product, of a moisturizing care product, of a BB (blemish balm) cream, a colored cream or foundation, a hair conditioning care product, a face and/or body cleansing product, a shower gel or a shampoo.

The present invention also relates to a non-therapeutic cosmetic method for makeup, hygiene, cleansing and/or care of the body and/or the hair comprising a step for applying on the skin at least one layer of a cosmetic composition according to the invention.

In all the application, the expression «comprising one» or «including one» means «comprising at least one» or «including at least one», i.e., «comprising one or more» or «including one or more», unless specified otherwise.

In the whole description above, unless mentioned otherwise, the term of «comprised between x and y» or «ranging from x to y» corresponds to an inclusive range, i.e., the values x and y are included in the range.

It was advantageously shown that the cosmetic compositions according to the invention are stable in a wide temperature range. This is notably related to the association of spiculisporic acid with at least one non-sulfate and non-sulfonate surfactant, and to the minimum salification level such that a base is present at a molar ratio $R_1$ (base: spiculisporic acid) strictly greater than 1 and preferentially less than or equal to 2.5.

Moreover, the stability of the compositions according to the invention are advantageously improved by associating spiculisporic acid with at least one non-sulfate and non-sulfonate surfactant in a mass ratio $R_2$ (spiculisporic acid:surfactant(s)) of about 2.5.

EXAMPLES

Suppliers
Spiculisporic acid: IWATA CHEMICAL

Example 1: Solubility of Spiculisporic Acid Alone

In order to neutralize spiculisporic acid (S-acid), two moles of base were used for one mole of S-acid, i.e., $R_1=2$.
The mass of base to be used for forming the di-substituted salt of the acid S is defined in the following way:

$$mass_{(base)}g = 2 \times \frac{mass_{(S\text{-}acid)}g}{MM_{(S\text{-}acid)}g \cdot mol^{-1}} \times MM_{(base)}g \cdot mol^{-1}$$

TABLE 1

Molecular formulae and molecular masses of the molecules of interest

|  | Molecular formula | Molar mass (g · mol$^{-1}$) |
| --- | --- | --- |
| Spiculisporic acid | $C_{17}H_{28}O_6$ | 328.4 |
| Sodium hydroxide | NaOH | 40 |
| Potassium hydroxide | KOH | 56.1 |

Increasing concentration ranges of S-acid from 1% to 10% were achieved, either with NaOH (solution at 30% m/m), or with KOH (solution at 50% m/m).

The solutions were made twice (A and B) in order to evaluate the reproducibility of the results. All the ranges of the neutralized solutions with both bases are limpid at $t_0$ and the pH values obtained range from 5.19 to 6.79.

TABLE 2

Values of the pHs and aspects of the S-acid solutions neutralized with NaOH (30%) and KOH (50%) stabilized at 4° C. and at RT.

| | S-acid. | 1 | | 2 | |
| --- | --- | --- | --- | --- | --- |
| Base | (%) | A | B | A | B |
| NaOH | pH T$_{RT\,t0}$ | 5.66 | 5.37 | 5.64 | 5.6 |
| solution at | pH T$_{RT\,24\,h}$ | 5.78 | 5.49 | 5.7 | 5.74 |
| 30% | pH T$_{4°\,C.\,24\,h}$ | 5.78 | 5.49 | 5.7 | 5.78* |
| | pH T$_{RT\,30\,days}$ | 5.59 | 5.42 | 5.64 | 5.49* |
| | pH T$_{4°\,C.\,30\,days}$ | 5.69 | 5.41 | 5.72* | 5.69* |
| KOH | pH T$_{RT\,t0}$ | 5.93 | 5.22 | 5.4 | 5.19 |
| solution at | pH T$_{RT\,24\,h}$ | 6.03 | 5.28 | 5.67 | 5.59* |
| 50% | pH T$_{4°\,C.\,24\,h}$ | 6.09 | 5.26 | 5.48 | 5.61* |
| | pH T$_{RT\,30\,days}$ | 5.69 | 5.18 | 5.39 | 5.59* |
| | pH T$_{4°\,C.\,30\,days}$ | 5.86 | 5.39 | 5.46* | 5.53* |

The marked solutions (*) correspond to precipitated solutions.

The stabilities of these solutions (table 2) show crystallization after 30 days at 4° C. from 2% of S-acid for both bases.

Example 2: Solubility of Spiculisporic Acid in Association with a Surfactant

Solutions, containing S-acid at 4% or 8% (neutralized with an amount of KOH calculated in order to obtain the di-potassium salt of S-acid, i.e., $R_1=2$) and surfactants, were made.

TABLE 3

Aspects and values of pH of solutions of the pre-solubilized S-acid with KOH in association with different families of surfactants.

| Name | Classification | compound (% of active material) | Acid S (% MA) | pH t0 RT | pH RT | 20 days after storage pH T = 4° C. |
| --- | --- | --- | --- | --- | --- | --- |
| S-acid alone | Anionic | — | 8 | 6.43 | 6.47 | 6.47* |
| S-acid alone | Anionic | — | 4 | 5.97 | 6.02 | 6.01* |
| Acid/surfactant associations | | | | | | |
| Lauryl betain (and) sodium chloride (sold under the name empigen BB/LS by Huntsman) | Amphoteric | 4 | 4 | 7.06 | 7 | 7.06 |
| Cocamidopropyl-betain (sold under the name Empigen Total Active TC/U by Huntsman) | Amphoteric | 4 | 4 | 7.03 | 6.93 | 7 |
| Disodiumcocoampho-diacetate (sold under the name Miranol C2M conc NP by Rhodia) | Amphoteric | 4 | 4 | 7.88 | 7.98 | 8.12 |
| coco-glucoside (sold under the name plantacare 818 UP by cognis) | Non-ionic | 4 | 4 | 6.67 | 6.72 | 6.72 |
| Decyl glucoside (sold under the name Plantacare 2000 UP by Cognis) | Non ionic | 4 | 4 | 6.91 | 6.92 | 6.99 |
| sucrose laurate (and) sorbitol (sold under the name Napture O gel V by sensient) | Non ionic | 4 | 4 | 6.45 | 6.46 | 6.48 |
| Disodium cocoyl glutamate (sold under the name Plantapon ACG HC by cognis) | Anionic | 4 | 4 | 8.3 | 7.68 | 8.29 |
| Sodium lauryl sarcosinate (sold under the name Sarkosyl NL 97 by Ciba Geigy) | anionic | 4 | 4 | 6.82 | 6.88 | 6.88 |
| Comparative examples | | | | | | |
| Sodium lauryl sulfate (sold under the name Tensopol A 795 by Tensachem) | anionic | 4 | 4 | 7.05* | 6.51* | 6.52* |
| Sodium lauryl methyl isethionate (sold under the name Iselux by Innospec Active Chemicals) | anionic | 4 | 4 | 6.38 | 6.44 | 6.46* |

Macroscopic observation gave the possibility of showing that the solution marked with (*) exhibited a precipitate, the other solutions being limpid.

The results of table 3 showed that after 20 days of storage at 4° C.:

precipitation of S-acid alone at 4% and 8%;
precipitation of the associations with sulfate and sulfonate anionic surfactants: sodium lauryl sulfate and sodium isethionate,
sharp improvement in the solubility of the associations with the other surfactants.

Solutions, containing S-acid at 4% or 8% (neutralized with an amount of NaOH calculated in order to obtain $R_1=1.1$) and surfactants, were made, as shown in the table below:

| Name | Classification | $R_1$ | Acid S (% MA) | pH t0 RT | Macroscopic observation after 12 days after storage |
|---|---|---|---|---|---|
| S-acid alone | Anionic | — | 8 | 5.11 | precipitate |
| S-acid alone | Anionic | — | 4 | 4.89 | precipitate |
| Lauryl betain (and) sodium chloride (sold under the name empigen BB/LS by Huntsman) | Amphoteric | | | | |
| Cocamidopropylbetain (sold under the name Empigen Total Active TC/U by Huntsman) | Amphoteric | 1.1 | 4 | 5.41 | limpid |
| Decyl glucoside (sold under the name Plantacare 2000 UP by Cognis) | Non ionic | 1.1 | 4 | 5.16 | limpid |
| Disodium cocoyl glutamate (sold under the name Plantapon ACG HC by cognis) | Anionic | 1.1 | 4 | 5.98 | limpid |
| Sodium lauryl sarcosinate (sold under the name Sarkosyl NL 97 by Ciba Geigy) | anionic | 1.1 | 4 | 5.65 | limpid |

The solutions were prepared according to the following procedure:

S-acid aqueous solution is prepared. The base is added under stirring. The resulting mixture is stirred at 40° C. Then the surfactant is added under stirring. The solution is then stored in the dark at 4° C.

The results showed that after 12 days of storage at 4° C.:
there is precipitation of S-acid alone at 4% and 8% of active material;
compositions comprising a surfactant according to the invention are limpid.

A clearly improved solubility and compatible with the cosmetic products of S-acid in an aqueous solution was shown under notably unfavorable temperature conditions (4° C.) by means of the association with specific surfactants and as base NaOH and KOH.

Example 3 (Comparative): Cosmetic Composition of Example 2 of JP 2002-47137

The Example 2 of JP 2002-47137 was reproduced

| INCI name | Formula on 100 g | Phases |
|---|---|---|
| Water | 90.60 | A |
| S-acid | 3.00 | A |
| KOH (solution with 50% of active material) | 0.90 | A |
| Hydroxypropylcellulose | 0.50 | B |
| Propylene glycol | 5.00 | B |

In the Example 2 of JP 2002-47137, there is no base for neutralizing the S-acid.

Example 3 was produced under the conditions of the Example 2 of JP 2002-47137 and with an amount of KOH equal to the one in Table 1 of JP 2002-47137, i.e.: 0.3% of pure KOH for 2% of S-acid (by mass).

The operating method is the following:
phase A was heated to 40° C. with stirring;
phase B was prepared by dispersing hydroxypropylcellulose in propylene glycol; and
phase B was poured into phase A.

One waited for at least 45 minutes, for total hydration of the cellulose.

The stability of the obtained composition was studied at 4° C.:

| | Aspect |
|---|---|
| $T_{RT} t_{24H}$ | Transparent slightly thickened aqueous solution |
| $T_{RT} t_{5\ days}$ | Transparent slightly thickened aqueous solution → No recrystallization |
| $T_{4°C.} t_{5\ days}$ | Opaque white slightly thickened aqueous solution → recrystallization |

Thus, this example shows that the composition comprising spiculisporic acid in the absence of any surfactant, and with a number of moles of KOH of less than once the number of moles of S-acid, is not stable at low temperatures.

Example 4 (Comparative): Cosmetic Composition of Example 3 of JP 2002-47137

The Example 3 of JP 2002-47137 was reproduced. This example applies a composition comprising:
the S-acid;
the dipropylene glycol;
the Tween 20 (Polysorbate 20 or polyoxyethylene sorbitan (20EO) monolaurate);
perfume/preservative/collagen.

In Example 3 of JP 2002-47137, there is no base for neutralizing the S-acid.

The tests 1 to 5 of the following table 4 were conducted under the conditions of Example 3 of JP 2002-47137 and with an amount of KOH equal to the one in Table 1 of JP 2002-47137, i.e.: 0.3% of pure KOH for 2% of S-acid (by mass). These amounts correspond to a KOH/S-acid molar ratio of the order of 0.88. The tests 1 to 5 were conducted with different ratios of the S-acid and of Polysorbate 20 (from 90:10 to 50:50).

On the other hand, the tests 6 to 8 of the following table 4 were conducted with a greater amount of KOH, so as to have 2 moles of KOH for 1 mole of S-acid, since, as experienced, the KOH level in table 1 of JP 2002-47137 is insufficient for maintaining good solubility.

S-acid of patent JP 2002-47137, there is an observable recrystallization for Example 3 of JP 2002-47137 and the compositions of tests 1 and 2. On the other hand, there was no recrystallization from the S-acid:Tween 20 mass ratio of 70:30 (from test 3), under the neutralization conditions of JP 2002-47137.

Once again, no recrystallization was observed for tests 6 to 8 with a KOH:S-acid molar ratio equal to 2.

After two weeks at 4° C., under neutralization conditions of patent JP 2002-47137, the whole of the compositions of tests 1 to 5 precipitates. However, it was noted that a decrease in the volume of precipitate occurred with decrease of the S-acid:Tween 20 mass ratio. At 4° C., the ratio 50:50 does not solve completely the problem of recrystallization but improves it.

TABLE 4

| | Comparative tests | | | | | | | | |
|---|---|---|---|---|---|---|---|---|---|
| Compound | Example 3 Patent JP 2002-47137 | Test 1 | Test 2 | Test 3 | Test 4 | Test 5 | Test 6 | Test 7 | Test 8 |
| SPICULISPORIC ACID (g) | 2.5 | 2.43 | 2.16 | 1.89 | 1.62 | 1.35 | 2.5 | 1.89 | 1.35 |
| POLYSORBATE 20 (g) | 0.2 | 0.27 | 0.54 | 0.81 | 1.08 | 1.35 | 0.2 | 0.81 | 1.35 |
| KOH (g) | 0.75 | 0.73 | 0.65 | 0.57 | 0.49 | 0.41 | 1.71 | 1.29 | 0.92 |
| DIPROPYLENE GLYCOL (g) | 3 | 3 | 3 | 3 | 3 | 3 | 3 | 3 | 3 |
| WATER (g) | 93.55 | 93.57 | 93.65 | 93.73 | 93.81 | 93.89 | 92.59 | 93.01 | 93.38 |
| KOH level | Idem from Table 1 of patent JP 2002-47137 (KOH: S-acid ratio (moles) = 0.88) | Idem from Table 1 of patent JP 2002-47137 (KOH: S-acid ratio (moles) = 0.88) | Idem from Table 1 of patent JP 2002-47137 (KOH: S-acid ratio (moles) = 0.88) | Idem from Table 1 of patent JP 2002-47137 (KOH: S-acid ratio (moles) = 0.88) | Idem from Table 1 of patent JP 2002-47137 (KOH: S-acid ratio (moles) = 0.88) | Idem from Table 1 of patent JP 2002-47137 (KOH: S-acid ratio (moles) = 0.88) | KOH: acid S ratio (moles) = 2 | KOH: acid S ratio (moles) = 2 | KOH: acid S ratio (moles) = 2 |
| Total TA (%) MA = MP | 2.70 | 2.70 | 2.70 | 2.70 | 2.70 | 2.70 | 2.70 | 2.70 | 2.70 |
| S-acid (%) | 92.59 | 90.00 | 80.00 | 70.00 | 60.00 | 50.00 | 92.59 | 70.00 | 50.00 |
| Polysorbate 20 (%) | 7.41 | 10.00 | 20.00 | 30.00 | 40.00 | 50.00 | 7.41 | 30.00 | 50.00 |
| pH 3 days at RT | 4.63 | 4.64 | 4.61 | 4.6 | 4.6 | 4.6 | 6.28 | 7.23 | 6.46 |
| Observation after 3 days at RT | Crystals | Crystals | Crystals | Limpid | Limpid | Limpid | limpid | Limpid | Limpid |
| Observation after 2 weeks at RT | Crystals | Crystals | Crystals | Limpid | Limpid | Limpid | Limpid | Limpid | Limpid |
| Observation after 2 weeks at 4° C. | Crystals | Crystals | Crystals | Crystals | Crystals | Crystals | Limpid | Limpid | Limpid |
| Observation after 60 days at RT | Crystals | Crystals | Crystals | Limpid | Limpid | Limpid | Limpid | Limpid | Limpid |
| Observation after 60 days at 4° C. | Crystals | Crystals | Crystals | Crystals | Crystals | Crystals | Limpid | limpid | Limpid |

Thus, it was shown that after 3 days at RT, the composition corresponding to Example 3 of JP 2002-47137, as well as the two compositions of tests 1 and 2 (with the 90:10 and 80:20 ratios) already have crystals. Thus, these compositions are not stable after 3 days at RT.

It was also shown that the addition of Tween 20 in an S-acid:Tween 20 mass ratio strictly less than 80:20 gives the possibility at this stage of avoiding recrystallization of the S-acid.

Finally, no recrystallization was observed for tests 6 to 8 with a KOH:S-acid molar ratio equal to 2.

Further, Table 4 also indicates that after two weeks and 60 days at RT and under conditions for neutralizing the Under identical preservation conditions, on the other hand, no recrystallization was observed for the tests 6 to 8.

As a conclusion of these comparative tests, it was shown that the conditions of Example 3 of JP 2002-47137 (S-acid:Tween 20 mass ratio 90:10, and the use of 0.88 mole of KOH for 1 mole of S-acid) are not adequate since S-acid re-precipitates both at RT and at 4° C.

However, the tests 6 to 8, conducted in a minimum salification level such that the number of moles of base is strictly greater than the number of moles of S-acid, lead to more stable compositions at RT than at 4° C.

Example 5: Cosmetic Product

| Phase | Constituents | % by weight | | | | | | | |
|---|---|---|---|---|---|---|---|---|---|
| Phase A | Water | 79.44 | 80.07 | 81.01 | 85.08 | 85.22 | 79.44 | 79.44 | 83.47 |
| Phase B | S Acid (100% MA) | 4 | 4 | 4 | 4 | 4 | 4 | 4 | 4 |
| | KOH (50% m/m) | 2.73 | 2.73 | 2.73 | 2.73 | 2.73 | 2.73 | 2.73 | 2.73 |
| | Lauryl betain (and) NaCl (30% MA) (sold under the name empigen BB/LS by Huntsman) | 13.33 | | | | | | | |
| | Disodium cocamphodiacetate (31.5% MA) (sold under the name Miranol C2M Conc NP) | | 12.7 | | | | | | |
| | Cocamidopropyl betain (34% MA) (sold under the name Empigen Total Active TC/U by Huntsman) | | | 11.76 | | | | | |
| | coco-glucoside (52% MA) (sold under the name plantacare 818 UP by cognis) | | | | 7.69 | | | | |
| | decyl-glucoside (53% MA) (sold under the name Plantacare 2000 UP by Cognis) | | | | | 7.55 | | | |
| | Sucrose laurate and sorbitol (30% MA) (sold under the name Natpure O Gel V by Sensient) | | | | | | 13.33 | | |
| | sodium lauroyl sarcosinate (30% MA) (sold under the name Sarkosyl NL 97 by Ciba Geigy) | | | | | | | 13.33 | |
| | disodium cocoyl glutamate (43% MA) (sold under the name Plantapon ACG HC by cognis) | | | | | | | | 9.3 |
| Phase C | Preservatives | 0.5 | 0.5 | 0.5 | 0.5 | 0.5 | 0.5 | 0.5 | 0.5 |

Phase A was heated to 40° C. After solubilization of S-acid, phase B was added to phase A. Next, phase C was added after phase B.

A portion of the solution was stored at room temperature and the other portion at 4° C.

It was observed that the obtained formulations are stable.

Example 6: Cosmetic Product—Emulsion

| Phase | Ingredients | Amounts |
|---|---|---|
| A | Water | 70.4 |
| A | Spiculisporic acid | 1 |
| A | KOH 50% (w/w) | 2 |
| A | Hydrogenated lecithin | 1 |
| A | Glycerine | 5 |
| A | Xanthan gum (RHODICARE CFT from Rhodia) | 0.2 |
| A | Benzyl alcohol | 0.6 |
| B | *simmondsia chinensis* oil (JOJOBA OIL GOLDEN ORGANIC from Desert Whale) | 6.6 |
| B | Dicaprylic ether | 6.6 |
| B | Mixture comprising a majority of n-undecane n-tridecane as prepared according to application WO2008/155059 | 6.6 |

In the main beaker: the spiculisporic acid was added to the water at a temperature comprised between 50° C. and 60° C. The KOH was added for neutralizing spiculisporic acid, and then hydrogenated lecithin was added. Xanthan gum was pre-dispersed in glycerin and the whole was added into the main beaker, before adding the preservative. The fatty phase was then heated to 60° C.

The emulsion was made at 60° C. with a RAYNERI rotor-stator and the speed was gradually increased up to 3,000 rpm. The emulsification was achieved at this speed for 5 minutes.

Characteristics of the Emulsion:
pH: 5.5
Stability: stable after 1 month at 45° C. and 4° C. (no recrystallization)
Viscosity: 14.6 UD (Rhéomat RM 200 NEUTREK, mobile MS-R2 viscosimeter)

The invention claimed is:

1. A cosmetic composition comprising, in a physiologically acceptable medium:
   an aqueous phase,
   spiculisporic acid,
   at least one non-sulfate and non-sulfonate surfactant selected from the group consisting of
      an anionic surfactant selected from the group consisting of (C6-C30)acylaminoacids, salts thereof and mixtures thereof,
      an amphoteric surfactant selected from the group consisting of: (C8-C20)alkylbetaines, sulfobetaines, (C8-C20)alkylsulfobetaines, (C8-C20)alkylamido (C1-C6)alkylbetaines, (C8-C20)alkylamido(C1-C6) alkylsulfobetaines, amino acids, (C8-C20)alkyl polyaminocarboxylates, (C8-C20)alkylamphoacetates, (C8-C20)alkylamphodiacetates, lecithins, salts thereof, and mixtures thereof, and
      a non-ionic surfactant selected from the group consisting of (C6-C30)alkyl polyglucosides, (C6-C30)alkylpolypentosides, (C6-C30)alkylpolyxylosides, maltose (C6-C30)esters, sucrose (C6-C30)esters, polyglycerol (C6-C30)fatty acids, oxyalkylene sugar esters, esters of (C6-C30)fatty acid and polyethylene glycol, esters of (C6-C30)fatty acid and sorbitan, ethyl-2 hexyl oxy-carbonyl N-methyl glucamine, and mixtures thereof;
   and
   at least one base selected from the group consisting of inorganic bases and basic amino acids, wherein the ratio $R_1$ of the number of moles of base over the number of moles of spiculisporic acid is strictly greater than 1, and wherein the ratio $R_2$ of the mass of spiculisporic acid over the mass of said surfactant is from 1 to 12.5; and wherein the composition does not include a surfactant comprising a sulfate and/or a sulfonate group.

2. The cosmetic composition according to claim 1, wherein the ratio $R_1$ is strictly greater than 1 and less than or equal to 2.5.

3. The cosmetic composition according to claim 1, wherein the ratio $R_2$ of the mass of spiculisporic acid over the mass of surfactant(s) is from 1 to 5.

4. The cosmetic composition according to claim 1, wherein the amphoteric surfactant is selected from the group consisting of cocoyl betain, cocamidopropylbetain, disodium cocoamphodiacetate, sodium cocoamphoacetate and mixtures thereof.

5. The cosmetic composition according to claim 1, wherein the anionic surfactant is selected from the group consisting of disodium cocoyl glutamate, sodium lauryl sarcosinate and mixtures thereof.

6. The cosmetic composition according to claim 1, wherein the non-ionic surfactant is selected from the group consisting of decyl glucoside, coco-glucoside, sucrose laurate, sorbitol, polyoxyethylene (20 EO) sorbitan monolaurate (Polysorbate 20), and mixtures thereof.

7. The cosmetic composition according to claim 1, wherein the base is selected from the group consisting of arginine, potassium hydroxide, sodium hydroxide and mixtures thereof.

8. The cosmetic composition according to claim 1, wherein spiculisporic acid is present in a content ranging from 0.1% to 15% by mass based on the total mass of said composition.

9. The cosmetic composition according to claim 1, wherein the total content of surfactant(s) ranges from 0.1% to 30% by mass based on the total mass of said composition.

10. A non-therapeutic cosmetic process for makeup, hygiene, cleansing and/or care of the skin and/or the hair comprising a step for applying on the skin at least one layer of a composition according to claim 2.

11. A non-therapeutic cosmetic method for makeup, hygiene, cleansing and/or care of the skin and/or of the hair comprising a step for applying on the skin at least one layer of a composition according to claim 1.

12. The cosmetic composition according to claim 2, wherein the ratio $R_2$ of the mass of spiculisporic acid over the mass of surfactant(s) from 1 to 5.

* * * * *